United States Patent [19]

Schmitt

[11] Patent Number: 5,559,851
[45] Date of Patent: Sep. 24, 1996

[54] X-RAY DIAGNOSTIC INSTALLATION HAVING A SCATTERED RADIATION GRID MOVEABLE IN A PLANE

[75] Inventor: Thomas Schmitt, Forchheim, Germany

[73] Assignee: Siemens Aktiengesellschaft, Munich, Germany

[21] Appl. No.: 374,027

[22] Filed: Jan. 18, 1995

[30] Foreign Application Priority Data

Jan. 24, 1994 [DE] Germany ............ 44 01 939.4

[51] Int. Cl.$^6$ .................................. G01N 23/04
[52] U.S. Cl. .................................. 378/155; 378/154
[58] Field of Search ................ 378/154, 155, 378/145

[56] References Cited

U.S. PATENT DOCUMENTS

| | | | |
|---|---|---|---|
| 2,062,562 | 12/1936 | Dent | 378/155 |
| 3,660,660 | 5/1972 | Pearson | 378/155 |
| 4,096,391 | 6/1978 | Barnes . | |
| 4,380,086 | 4/1983 | Vagi . | |
| 4,646,340 | 2/1987 | Bauer | 378/155 |
| 4,731,806 | 3/1988 | Takahata | 378/155 |
| 5,305,369 | 4/1994 | Johnson et al. | 378/155 |

FOREIGN PATENT DOCUMENTS

| | | | |
|---|---|---|---|
| 0402082 | 12/1990 | European Pat. Off. . | |
| 1034561 | 7/1953 | France | 378/155 |

*Primary Examiner*—David P. Porta
*Attorney, Agent, or Firm*—Hill, Steadman & Simpson

[57] ABSTRACT

In an x-ray diagnostics apparatus having a scattered radiation grid moveable in a plane, the movement of the scattered radiation grid ensues via a tumbling or wobble bearing arranged between a rotating drive and the scattered radiation grid. An advantage of this arrangement is that relatively long standstill times during the reversal of the grid movement are reduced. Moreover, the tumbling or wobble bearing can be economically manufactured and is less structurally complicated than a lever articulation.

8 Claims, 1 Drawing Sheet

X-RAY DIAGNOSTIC INSTALLATION HAVING A SCATTERED RADIATION GRID MOVEABLE IN A PLANE

BACKGROUND OF THE INVENTION

1. Field of the Invention

The present invention is directed to an x-ray diagnostic installation of the type having a scattered radiation grid, and in particular a scatter radiation grid which is moveable in a plane.

2. Description of the Prior Art

European Application 0 402 082 A1 and U.S. Pat. No. 4,380,086 disclose respective x-ray diagnostic apparatuses having scattered radiation grids adjustable in a plane by means of a rotating drive. The conversion of the drive rotation into a reciprocating motion of the scattered radiation grid ensues via cams.

U.S. Pat. No. 4,096,391 discloses an x-ray diagnostic apparatus wherein a ray beam emitted by an x-ray tube is incident on a radiation receiver. An exposure subject can be arranged between the x-ray tube and the radiation receiver, so that the radiation receiver receives an x-ray shadowgram of the exposure subject. This x-ray shadowgram is converted into a visible image that, for example, can be displayed on a monitor. Scattered radiation arises upon transirradiation of the exposure subject, this scattered radiation disadvantageously influencing the visible image. A scattered radiation grid that absorbs the scattered radiation is therefore provided between the exposure subject and the radiation receiver for reducing the scattered radiation component. In order to avoid an imaging of the lamellae of the scattered radiation grid on the radiation receiver, an electro-mechanical drive is provided with which the scattered radiation grid is moved in a plane during the x-ray exposure. To this end, for example, an electromechanical can be employed that engages at the scattered radiation grid via a lever articulation. The lever arrangement is implemented such that it converts a rotating motion into a longitudinal motion.

A disadvantage of such a lever arrangement is the relatively long standstill times of the scattered radiation grid when it changes its movement direction when reciprocating from a first into a second direction.

SUMMARY OF THE INVENTION

It is an object of the present invention to implement an x-ray diagnostic apparatus of the type initially described such that these high standstill times are avoided.

This object is inventively achieved by an x-ray diagnostic apparatus having a scattered radiation grid moveable in a plane, wherein the adjustment ensues via a tumbling or wobble bearing arranged between a rotating drive and the scattered radiation grid.

An advantage of the invention is that such a tumbling or wobble bearing can be economically manufactured; moreover the dwell (standstill) times during the directional reversal are slight i.e., they are sufficiently short so as to preclude the imaging of the scattered radiation grid on the radiation receiver. Further, a tumbling or wobble bearing enables a high adjustment speed of the scattered radiation grid due to the low mass.

DESCRIPTION OF THE PREFERRED EMBODIMENTS

Figure 1:
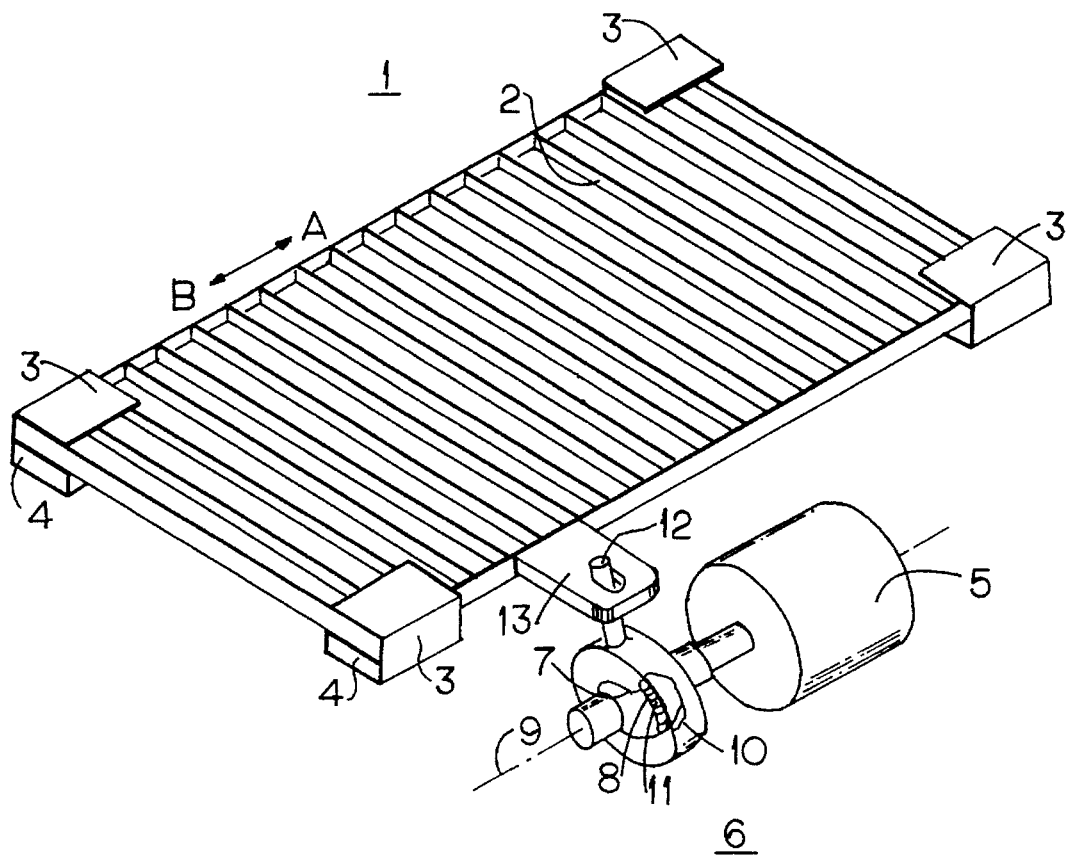
FIG. 1 is a perspective view of a scattered radiation grid and an apparatus for moving the scattered radiation grid constructed in accordance with the principles of the present invention, having a first embodiment of a wobble element.
Figure 2:
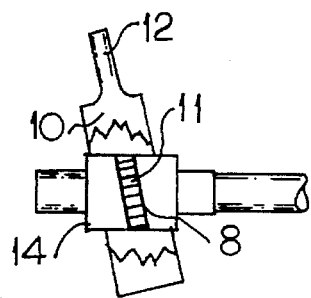
FIG. 2 is a side view, partly broken away, of a portion of the apparatus shown in FIG. 1, illustrating a second embodiment of a wobble element.

In FIG. 1, a scattered radiation grid is identified with reference numeral 1. This scattered radiation grid 1 has diaphragm lamellae 2 of radiation-absorbent material arranged parallel to one another that can be aligned onto the focus of a radiation transmitter. The scattered radiation grid 1 is movably seated at two guides 3 engaging sides lying opposite one another, and thus is seated so as to be moveable in a plane. The guides 3 can engage the scattered radiation grid 1 via rollers or plain bearings 4. A drive 5 that is coupled to a wobble bearing 6 is provided. The controllable, preferably electro-mechanical, drive 5 generates a rotating motion that is transmitted onto a spherical part 7 (or a cylindrical part 14 shown in FIG. 2) of the wobble bearing 6. A channel 8 that is aligned obliquely relative to the longitudinal axis of the spherical part 7 or cylindrical part 14 is provided at the circumference of the part 7. A housing 10 engages the channel 8 via ball bearings 11, with a peg 12 projecting from the housing 10 engaging an opening in a tab 13 of the scattered radiation grid 1 in the exemplary embodiment. Alternatively, an articulation or a bearing can be employed that produces a connection between the housing 10 and the scattered radiation grid 1. When the drive 5 is operated a rotational motion is converted via the wobble bearing 6 into a longitudinal displacement of the scattered radiation grid 1 in a plane and in directions A and B.

Within the scope of the invention, an articulation can also be aligned parallel to the longitudinal axis 9. This articulation engages at the channel of a spherical or cylindrical part via a peg, so that a rotational motion can also be converted into a longitudinal adjustment. The end of the articulation is thereby preferably held in a bushing guide. Differing from the first exemplary embodiment, the end of the articulation engages at the scattered radiation grid in the adjustment direction.

Although modifications and changes may be suggested by those skilled in the art, it is the intention of the inventor to embody within the patent warranted hereon all changes and modifications as reasonably and properly come within the scope of his contribution to the art.

I claim as my invention:

1. In an x-ray diagnostic apparatus having a scattered radiation grid, the improvement of means for reciprocatingly moving said scattered radiation grid comprising:

drive means having a drive shaft which rotates around a longitudinal axis;

a single wobble element mounted on said drive shaft for corotation therewith, said wobble element having an exterior surface with a single channel therein disposed in a plane oriented obliquely relative to said longitudinal axis; and non-articulated means mechanically interconnected between said single channel and said scattered radiation grid for following said single channel as said single wobble element is rotated converting rotational motion of said drive shaft into reciprocating motion of said scattered radiation grid in first and second directions with short standstill times of said radiation grid when changing between said first and second directions of movement.

2. The improvement of claim 1 wherein said non-articulated means comprises:

a housing surrounding said wobble element and engaging said channel so that said housing follows movement of said channel as said wobble element is rotated by said drive shaft;

a peg carried on an exterior of said housing;

and wherein said scattered radiation grid has a tab with an opening therein which receives said peg.

3. The improvement of claim 1 wherein said wobble element comprises a spherical element.

4. The improvement of claim 1 wherein said wobble element comprises a cylindrical element.

5. In an x-ray diagnostic apparatus having a scattered radiation grid, the improvement of means for reciprocatingly moving said scattered radiation grid comprising:

drive means having a drive shaft which rotates around a longitudinal axis;

a single wobble element mounted on said drive shaft for corotation therewith, said wobble element having an exterior surface with a single channel therein disposed in a plane oriented obliquely relative to said longitudinal axis; and non-articulated means mechanically interconnected between said single channel and said scattered radiation grid for following said single channel as said single wobble element is rotated converting rotational motion of said drive shaft into reciprocating motion of said scattered radiation grid.

6. The improvement of claim 5 wherein said non-articulated means comprises:

a housing surrounding said wobble element and engaging said channel so that said housing follows movement of said channel as said wobble element is rotated by said drive shaft;

a peg carried on an exterior of said housing;

and wherein said scattered radiation grid has a tab with an opening therein which receives said peg.

7. The improvement of claim 5 wherein said wobble element comprises a spherical element.

8. The improvement of claim 5 wherein said wobble element comprises a cylindrical element.

\* \* \* \* \*